(12) United States Patent
Patel (10) Patent No.: US 7,419,684 B2
(45) Date of Patent: Sep. 2, 2008

(54) SYSTEM AND METHOD FOR MANUFACTURING ORAL OSMOTIC DRUG DELIVERY DEVICES, AND METHODS OF ADMINISTERING SAME

(75) Inventor: Hasmukh B. Patel, Edison, NJ (US)

(73) Assignee: Reliant Pharmaceuticals, Inc., Liberty Corner, NJ (US)

( * ) Notice: Subject to any disclaimer, the term of this patent is extended or adjusted under 35 U.S.C. 154(b) by 0 days.

(21) Appl. No.: 11/615,163

(22) Filed: Dec. 22, 2006

(65) Prior Publication Data
US 2008/0152718 A1 Jun. 26, 2008

(51) Int. Cl.
A61K 9/24 (2006.01)
A61K 9/20 (2006.01)
A61K 9/22 (2006.01)
A61K 9/14 (2006.01)

(52) U.S. Cl. .................. 424/473; 424/464; 424/468; 424/472; 424/489

(58) Field of Classification Search .............. 424/472, 424/474, 2.16, 2.21, 19, 29; 427/2.16, 2.21; 702/19, 29
See application file for complete search history.

(56) References Cited

U.S. PATENT DOCUMENTS

| | | | |
|---|---|---|---|
| 4,612,008 A | | 9/1986 | Wong et al. |
| 4,816,263 A | * | 3/1989 | Ayer et al. |
| 4,946,687 A | | 8/1990 | Ayer et al. |
| 4,950,486 A | | 8/1990 | Ayer et al. |
| 4,992,278 A | | 2/1991 | Khanna |
| 5,030,456 A | | 7/1991 | Ayer et al. |
| 5,232,705 A | | 8/1993 | Wong et al. |
| 5,543,155 A | | 8/1996 | Fekete et al. |
| 6,096,339 A | | 8/2000 | Ayer et al. |
| 6,514,530 B2 | | 2/2003 | Skluzacek et al. |
| 6,630,165 B2 | | 10/2003 | Seroff et al. |
| 2005/0169992 A1 | | 8/2005 | Jao et al. |
| 2006/0031024 A1 | | 2/2006 | Mountassir .................. 702/19 |
| 2006/0078621 A1 | | 4/2006 | Wedinger et al. ............ 424/489 |
| 2006/0100786 A1 | * | 5/2006 | Choi |
| 2006/0210623 A1 | | 9/2006 | Stach et al. .................. 424/457 |

FOREIGN PATENT DOCUMENTS

WO   WO 2006046114 A2   5/2006

OTHER PUBLICATIONS

Shubair, MS, "Effect of granules properties on the in-vitro and in-vivo performance of ibuprofen sustained release matrix tablets." Scientia Phamaceutica 72(4):317-322 (2004).*

Gudsoorkar, VR, et al., "Influence of process variables on drug release from disintegrating type sustained release ibuprofen tablets." Eastern Pharmacist 40(471):111-113 (1997).*

Arulsudar, N. et al. "Comparison of artificial neural network and multiple linear regression in the optimization of formulation parameters of leuprolide acetate loaded liposomes." J. Pharm. Pharmaceut. Sci. 8(2):243-258 (2005).*

S.V. Sastry et al. "Aqueous based polymeric dispersion:Plackett-Burman design for screening of formulation variables of Atenolol Gastrointestinal Therapeutic System" Pharmaceutica Acta Helvetiae 73; 105-112 (1998).*

Shubair, MS, "Effect of granules properties on the in-vitro and in-vivo performance of ibuprofen sustained release matrix tablets." Scientia Pharmaceutica 72(4):317-322 (2004) (complete copy).

Gudsoorkar, VR, et al., "Influence of process variables on drug release from disintegrating type sustained release ibuprofen tablets." Eastern Pharmacist 40(471):111-113 (1997) (complete copy).

Tardos et al., "Critical parameters and limiting conditions in binder granulation of fine powders," Powder Technology, 94, 1997, pp. 245-258.

Schaefer et al., "Control of fluidized bed granulation," Arch. Pharm. Chem. Sci. Ed., 5, 1977, pp. 51-60.

Schaefer et al., "Control of fluidized bed granulation," Arch. Pharm. Chem. Sci. Ed., 6, 1978, pp. 1-13.

Ennis "Theory of Granulation: An Engineering Perspective," Hanbook of Pharmaceutical Granulation Technology, 2$^{nd}$ Ed, 2005, pp. 7-78.

Gokhale et al., "High-Shear Granulation," Handbook of Pharmaceutical Granulation Technology, 2$^{nd}$ Ed, 2005, pp. 191-228.

Rekhi et al., "Sizing of Granulation," Handbook of Pharmaceutical Granulation Technology, 2$^{nd}$ Ed, 2005, pp. 491-512.

"Current Issues and Troubleshooting Fluid Bed Granulation," Pharmaceutical Technology (Europe), Publ. No. 00496, 1998, 5 pp.

Rantanen et al., "Process Analysis of Fluidized Bed Granulation," AAPS PharmSciTech 2(4):article 21 (2001).

Krishnamurthy "Study of Particle Growth and Particle Size Distributions in Batch Fluidised Bed Granulation," Chem. Eng. Dept, Chennai 600 036, India, 3 pp (2006).

(Continued)

*Primary Examiner*—Humera N Sheikh
(74) *Attorney, Agent, or Firm*—Arent Fox LLP (57) ABSTRACT

A system and method for manufacturing oral osmotic drug delivery devices including the use of a mathematical model in deriving relationships between parameters used in manufacturing the devices for a desired release rate of the active drug substance contained therein. The derived relationship is then used to control the parameters so that the active substance within the device is delivered at a desired rate. Methods of administering the oral osmotic drug delivery devices are also provided. Use of a mathematical model in deriving relationships between parameters used in the drug granulation process for a desired range of percentage fines of the drug granulation substance. The derived relationship is then used to control the parameters in the drug granulation process so that the desired percentage fines are obtained in the drug granulation substance.

11 Claims, 7 Drawing Sheets

OTHER PUBLICATIONS

Kristensen et al., "*Wet Granulation in Rotary Processor and Fluid Bed: Comparison of Granule and Tablet Properties,*" AAPS PharmSciTech 7(1):article 22 (2006).

"Sustained-Release Tablet via Direct Compression: A Feasibility Study Using Cellulose Acetate and Cellulose Acetate Butyrate." Found at http://www.eastman.com/NR/rdonlyres/31067BE2-D623-4C3A-B035-C5B8C81B29FB/0/EFC234.pdf. (2000).

"Eastman Cellulose Esters for Pharmaceutical Drug Delivery." Found at http://www.eastman.com/NR/rdonlyres/159C674E-6005-4F52-925C-7B4CFB00BF28/0/PCI105.pdf. (2005).

Haddish-Berhane, N, et al., "A multi-scale stochastic drug release model for polymer-coated targeted drug delivery systems." J. Control Release 110(2):314-322 (Jan. 10, 2006, electronically published Nov. 8, 2005) (Abstract Only).

Ansari, MA, et al., "Formulation of hollow core granules by fluid bed in situ melt granulation: modelling and experiments." Int. J. Pharm. 321(1-2):108-116 (Sep. 14, 2006, electronically published May 16, 2006) (Abstract Only).

Li, L, et al., "The application of an artifical neural network and pharmacokinetic models in the design of clozapine pH-independent tablets." Zhongguo Yaoxue Zazhi 40(17):1323-1326 (2005) (Abstract Only).

Shubair, MS, "Effect of granules properties on the in-vitro and in-vivo performance of ibuprofen sustained release matrix tablets." Scientia Pharmaceutica 72(4):317-322 (2004) (Abstract Only).

Gudsoorkar, VR, et al., "Influence of process variables on drug release from disintegrating type sustained release ibuprofen tablets." Eastern Pharmacist 40(471):111-113 (1997) (Abstract Only).

Ibric, S, et al., "Artificial Neural Networks in the Modeling and Optimization of Aspirin Extended Release Tablets with Eudragit L 100 as Matrix Substance." AAPS PharmSciTech 4(1):article 9 (2003).

Arulsudar, N, et al. "Comparison of artificial neural network and multiple linear regression in the optimization of formulation parameters of leuprolide acetate loaded liposomes." J. Pharm. Pharmaceut. Sci. 8(2):243-258 (2005).

U.S. Appl. No. 11/432,661, filed May 12, 2006. Inventor: Hasmukh B. Patel.

U.S. Appl. No. 11/432,670, filed May 12, 2006. Inventor: Hasmukh B. Patel.

U.S. Appl. No. 11/432,671, filed May 12, 2006. Inventor: Hasmukh B. Patel.

Dynacirc CR®, Reliant Pharmaceuticals, Inc., Aug. 2005, 2 pages.

"A Novel Pulsed Release System Based on Swelling and Osmotic Pumping Mechanism", Zhang et al, Journal of Controlled Release, 89 (2003), pp. 47-55.

"Aqueous Based Polymeric Dispersion: Plackett-Burman design for screening of formulation variables of Atenolol Gastrointestinal Therapeutic System", Pharmaceutica Acta Helvetiae, 73 (1998), pp. 105-112.

\* cited by examiner

SYSTEM AND METHOD FOR MANUFACTURING ORAL OSMOTIC DRUG DELIVERY DEVICES, AND METHODS OF ADMINISTERING SAME

BACKGROUND OF THE INVENTION

1. Field of the Invention

The present invention relates generally to a system and method for manufacturing oral osmotic drug delivery devices. In particular, the present invention is directed towards deriving a mathematical model of a relationship between parameters used in manufacturing the devices, using statistical analysis of historical data. The derived relationship may then be used to control the parameters so that the active drug substance within the product is delivered at a desired rate. The present invention also relates to methods of administering the oral osmotic drug delivery devices to subjects. The present invention further relates to methods of making particles of a drug and one or more excipients.

2. Description of Related Art

Unless conventional rapid acting drug therapy is carefully administered at frequent intervals to maintain an effective steady state level of the therapeutic agent or active substance, peaks and valleys in the level of the active drug in the patient's system can occur because of, for example, rapid absorption and systemic excretion of the compound and occurrence of metabolic inactivation, thereby producing special problems in maintenance therapy of the patient. This result can cause the active substance to be delivered to the patient's system in a dosage that may be too high and to regions of the body where the active substance may not be at its most effective.

These problems can be overcome to some extent by controlled release forms of the therapeutic agent or active substance. These forms are also referred to as controlled release sustained release, retarded release, and slow release.

Controlled release dosage ideally provides and maintains therapeutic concentrations of the active substance in the patient's system throughout the dosing interval with an acceptable peak/valley concentration ratio. Controlled release formulations are designed to provide a longer period of pharmacologic action after administration than is ordinarily obtained after administration of immediate-release dosage forms. Controlled release compositions may be used, for example, to maintain a desired concentration of said therapeutic agent in the patient's system for a longer duration than would occur if conventional rapid release dosage forms were to be administered. Such longer periods of response provide for therapeutic benefits that are not achieved with corresponding short acting, immediate release preparations. Thus, therapy may be continued without interrupting the sleep of a patient, for example, which can be of particular importance when treating a patient for moderate to severe pain, or for treating a debilitated patient for whom sleep is essential. A further general advantage of longer acting drug preparations is improved patient compliance resulting from the avoidance of missed doses through patient forgetfulness.

The benefits of controlling the release of the active ingredient to sustain a constant release over a predetermined amount of time include: improved delivery to the required site; improved delivery at the required rate by reducing swings of drug levels in the patient's system; allowing fewer doses per day; reduced dangers of overdosing; avoidance of side effects from rapid increases in drug concentration within a patient's system; prevention of drug concentration in the patient's system from dropping below therapeutic levels; and assurance of more efficient dosages. In order to accomplish these goals, the controlled release formulation must provide a reliable dissolution and release rate of the active substance.

In the past, the manufacturing process of controlled release tablets has not led to uniform release rates and dissolution of the active substance. Thus, the drug delivery rate can fall above or below the desired delivery rate. When the delivery rate for a controlled release tablet falls sufficiently outside the approved specifications, the tablet cannot be placed in the market to be used by a patient. Thus, it is necessary to have a manufacturing process that consistently produces tablets with a delivery rate of the active substance within the desired range and that is amenable to large scale manufacturing processes. It is also necessary to have a manufacturing process that allows for particles of the active substance and excipients to fall within specified, predetermined size limitations.

SUMMARY OF THE INVENTION

Among other things, the present invention provides systems and methods for manufacturing controlled release tablets that consistently provide a delivery rate within a predetermined range. Using statistical analysis of historical data a mathematical model is derived that defines a relationship between parameters used in manufacturing controlled release products. The derived relationship may then be used to select and control the parameters so that the active substance within the controlled release product is delivered at a desired rate and extent.

Thus, one embodiment of the invention is directed to a method of making an oral osmotic drug delivery device comprising collecting measurements on the amount of fines in the active layer (hereinafter also referred to as the "percentage fines"), a weight value of a plurality of bi-layer cores (hereinafter also referred to as the "pan load"), and a weight value of the outer coating (hereinafter also referred to as the "weight gain") used in manufacturing the plurality of osmotic drug delivery devices and determining a release rate for each of the plurality of osmotic drug delivery devices; deriving a relational mechanism relating the percentage fines, pan load, and weight gain used in manufacture of the osmotic drug delivery devices for a selected release rate using the collected measurements; selecting at least one parameter of percentage fines, pan load, and weight gain; and determining at least one of the remaining parameters to obtain the selected release rate in the osmotic drug delivery devices using the relational mechanism. Also included are an oral osmotic delivery device made by the method, and methods of delivering an oral osmotic delivery device made using the method to a subject in need thereof.

Another embodiment of the invention is directed to a method of making a plurality of oral osmotic drug delivery devices each of which comprises a bi-layer core comprising (1) an active layer comprising particles of a mixture of a drug and one or more excipients wherein the particles include an amount of fines, (2) an osmotic layer, and (3) a semi-permeable outer coating substantially surrounding the bi-layer core, the method comprising: manufacturing a plurality of oral osmotic drug delivery devices, collecting measurements on the amount of fines in the active layer, a weight value of a plurality of bi-layer cores, and a weight value of the outer coating used in the manufacturing of the plurality of osmotic drug delivery devices, and determining a release rate for each of the plurality of osmotic drug delivery devices; deriving a relational mechanism relating the amount of fines, the weight value of the plurality of bi-layer cores, and the weight value of the outer coating for a selected release rate using the collected measurements; selecting at least one parameter of the amount of fines, the weight value of the plurality of bi-layer cores, and the weight value of the outer coating; determining at least one of the remaining parameters to obtain the selected release rate in a further plurality of oral osmotic drug delivery devices using the relational mechanism; and manufacturing the further plurality of oral osmotic drug delivery devices utilizing information obtained from the determining step. Also included are oral osmotic delivery devices made by the method, and methods of delivering oral osmotic delivery devices made using the method to a subject in need thereof.

Another embodiment of the invention is directed to a method of once daily delivery of isradipine to a subject in need thereof, comprising administering once daily to the subject a plurality of oral osmotic drug delivery devices each of which comprises a bi-layer core comprising (1) an active layer comprising particles of a mixture of isradipine and one or more excipients wherein the particles include an amount of fines, (2) an osmotic layer, and (3) a semi-permeable outer coating substantially surrounding the bi-layer core, wherein the plurality of oral osmotic drug delivery devices is manufactured by a method whereby a selected release rate is obtained by applying a relational mechanism relating the amount of fines, a weight value of the plurality of bi-layer cores, and a weight value of the outer coating.

Another embodiment of the invention is directed to a method of making particles of a drug and one or more excipients, the method comprising: deriving a relationship between an electrical current level and/or a power level used in a mixing device for mixing a drug and excipients to produce particles, and a corresponding amount of fines obtained in the particles, wherein the current and the power of the mixing device vary as a function of the constituency of the substance being mixed; selecting a desired amount of fines; and determining, using the derived relationship, a current level and/or a power level that produces the desired amount of fines. Also included are particles of a drug and one or more excipients made by the method, and methods of delivering particles of a drug and one or more excipients made using the method to a subject in need thereof.

BRIEF DESCRIPTION OF THE DRAWINGS

For a more complete understanding of the present invention, the needs satisfied thereby, and the objects, features, and advantages thereof, reference now is made to the following description taken in connection with the accompanying drawings.

DETAILED DESCRIPTION OF PREFERRED EMBODIMENTS

Preferred embodiments of the present invention and their features and advantages may be understood by referring to FIGS. 1 through 9. The following references are incorporated by reference in their entirety: PAT initiative, http://www-.fda.gov/cder/OPS/PAT.htm; Guidance for Industry: PAT—Framework for Innovative Pharmaceutical Development, Manufacturing, and Quality Assurance. September 2004; "Sustained-Release Tablet via Direct Compression: A Feasibility Study Using Cellulose Acetate and Cellulose Acetate Butyrate" at http://www.eastman.com/NR/rdonlyres/31067BE2-D623-4C3A-B035-C5B8C81B29FB/0/EFC234.pdf; "Eastman Cellulose Esters for Pharmaceutical Drug Delivery" at http://www.eastman.com/NR/rdonlyres/159C674E-6055-4F52-925C-7B4CFB00BF28/0/PCI105.pdf; JMP 6.0 Software, SAS Institute, Cary, N.C.; and SAS 9.1 Software, SAS Institute, Cary, N.C.

Figure 1:
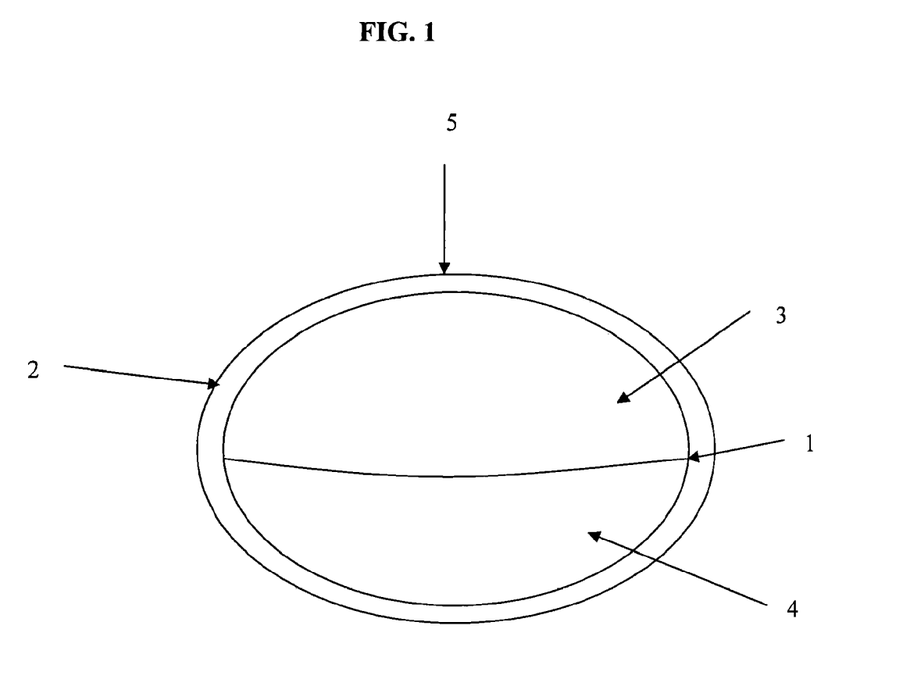
FIG. 1 shows a diagram of a controlled release tablet, in accordance with an embodiment of the present invention.

An exemplary embodiment of the present invention will now be described with reference to FIG. 1. An exemplary tablet manufactured in accordance with the method and system of the present invention includes a bi-layer core 1 substantially surrounded by a coating 2. The coating 2 is, for example, a water-insoluble, semi-permeable membrane coating, such as cellulose acetate. The bi-layer core 1 includes a layer having a water soluble therapeutic agent or pharmaceutically active substance and excipients, also interchangeably referred to herein as the "active layer" 3, and a layer including a substance that swells under the influence of water, also interchangeably referred to herein as the "osmotic layer" 4. The semi-permeable membrane coating has at least one opening 5 communicating with the active layer. This opening may be laser drilled, for example. The semi-permeable membrane may be surrounded by a soluble overcoating.

After an oral osmotic dosage form made in accordance with one or more of the embodiments of the present invention is administered to a patient, any soluble tablet overcoating is quickly dissipated in the gastrointestinal tract, allowing water to enter the tablet through the semipermeable membrane 2. The water-insoluble coating restrains the release of the active substance from the active layer. The osmotic layer 4 expands under the influence of water penetrating the coating. The at least one opening 5 allows the hydrated active substance in the active layer to be released as a fine suspension out of the tablet due to pressure from the swelling of the osmotic layer 4. The active substance may, for example, be in a gel form when hydrated with water, such as water that that penetrates the semi-permeable membrane. The biologically inert core of the tablet remains intact and is simply expelled later from the patient's body. An example of such a product can be found in U.S. Pat. No. 4,816,263, hereby incorporated by reference. The methods of administration in accordance with the embodiments of the present invention may provide a patient with a drug delivery rate that is essentially constant for a predetermined period of time, after which delivery typically gradually falls to a negligible amount, ensuring optimum release and dissolution rate characteristics. The methods of administration of the present invention may be beneficially used to treat any of a number of conditions that benefit from substantially constant drug delivery, e.g., hypertension.

The active substance that can be delivered from the oral osmotic drug delivery device preferably includes a member selected from the group consisting of anticonvulsants, analgesics, antiparkinsons, anti-inflammatories, calcium antagonists, anesthetics, antimicrobials, antimalarials, antiparasites, antihypertensives, antihistamines, antipyretics, alpha-adrenergic agonist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

In a preferred embodiment, the drug is represented by a member selected from the group of a calcium channel blocker such as nifedipine, isradipine, nilvadipine, verapamil, flunarizine, nimodipine, diltiazem, nicardipine, norverapamil, nitredipine, nisoldipine, felodipine, amlodipine, cinnarizine and fendiline. In other embodiments, the drug is represented by an angiotensin converting enzyme inhibitor selected from the group consisting of angiotensin converting enzyme inhibitors that are essentially-free of sulfur, angiotensin converting enzyme inhibitors containing a sulfhydryl group, angiotensin converting enzyme inhibitors containing a linear sulfide, angiotensin converting enzyme inhibitors containing a cyclic sulfide, and angiotensin converting enzyme inhibitors containing a methylsulfonyl group. Representation of angiotensin converting enzyme inhibitors are more specifically represented by a member selected from the group consisting of ramipril, fosinopril, altiopril, benazepril, libenzapril, alacepril, cilazapril, cilazaprilat, perindopril, zofenopril, enalapril, lisinopril, imidapril, spirapril, rentiapril, captopril, delapril, alindapril, indolapril, and quinapril.

It is preferable that drug delivery be essentially constant for a predetermined period of time, after which delivery typically gradually falls to a negligible amount. As discussed above, it is important that the controlled release tablets be manufactured by a system and process that consistently ensures optimum release and dissolution rate characteristics. In some embodiments, it is preferable that the release rate fall within a predetermined approved range of release rates, and it is preferred that the release rate be near the center of this approved range. In preferred embodiments of the invention, the release rate falls within 6.93%/hr to 9.12%/hr of the drug dose set forth in the label claim, preferably 7.03%/h to 9.02%/h, and more preferably ±10%, and most preferably ±5%, of 8.03%/hr. In other preferred embodiments of the invention, the 16 hour cumulative dissolution percentage (Q) is at least 80%, preferably at least 85%, more preferably at least 90%, of the drug dose set forth in the label claim.

At least the following three factors affect the release rate of the finished controlled release tablet: (1) the weight gain of the tablet coating; (2) the percentage of fines in the active substance layer; and (3) the pan load of uncoated bi-layer cores. Each of these factors may be varied in a relative manner so as to meet predetermined tablet release characteristics, as will be described further below.

The weight gain of the tablet coating is the thickness or amount of the membrane coating applied per tablet. The weight gain may be measured by measuring the weight of a predetermined number of uncoated bi-layer cores in a pan before they are coated and, at intervals during the coating process, measuring the weight of the same number of tablets in the pan. The physio-chemical nature of the coating also influences this factor.

The percentage of fines in the active layer is a measure of the physical composition of the active substance in the active layer. The particle size of the particles composed of the therapeutic agent and excipients in the active layer contributes to the release rate of the finished tablet. The particle size is measured as the percentage of the granules or fines that are able to pass through a predetermined mesh size, also interchangeably referred to herein as "percentage of fines" or "PctFines." One exemplary embodiment of this measure includes determining the percentage of particles in the active layer that pass through a #120 mesh screen, and are then collectable over a #200 mesh screen and the pan. See U.S. patent application Ser. Nos. 11/432,670; 11/432,671; and 11/432,661, each hereby incorporated by reference.

The pan load is a measure of the number of uncoated bi-layer cores per pan. In the process of coating the tablets, a large number of tablets are simultaneously coated by placing the unfinished tablets together in a rotating pan. The pan rotates the tablets while they are sprayed with a coating, such as acetone with cellulose acetate. The pan load is the weight of the unfinished tablets in the rotating pan, as a way of quantifying the number of tablets in the rotating pan.

Implementation of the method and system of the present invention includes applying a mathematical model derived using statistical analysis of historical data for a particular active substance having a predetermined optimal release rate. A table is produced from this model, based on the influence of the PctFines, pan load, and membrane (coating) weight gain. The table is then cross-referenced for use in controlling the manufacturing parameters of the controlled release tablet so as to maintain the optimal release rate.

For example, once the table is defined, if two of three influencing parameters are predetermined and held constant, the third parameter can be determined during manufacture of the controlled release tablet to ensure the optimal release rate. Similarly, if one parameter is constant and a second parameter varies, the third parameter may be varied so as to maintain the optimal release rate of the manufactured controlled release tablets.

In one exemplary embodiment, the PctFines and the pan load are predetermined and kept constant, and the release rate may then be controlled by altering the weight gain parameter, so as to meet the required release rate.

The mathematical model can be derived using any one of multiple linear regression, a neural network, local regression such, as a LOESS model, or Monte Carlo simulation. In one embodiment, a LOESS model is used in connection with a sufficient amount of historical data to derive an accurate table.

The historical data includes measures of a release rate for a plurality of controlled release tablets, preferably a plurality of batches of controlled release tablets, including a particular active substance, along with the corresponding measures of at least the PctFines, the pan load, and the membrane weight gain. An exemplary embodiment of historical data for 5 mg and 10 mg controlled release isradipine tablets (marketed under the name DYNACIRC CR®) is shown in Table 1. This data includes the 16 hour cumulative dissolution percentage, Q; the release rate, RR; the percentage of fines, PctFines; the membrane weight gain, WtGain; the spray time of the coating; and the pan load, PanWt. The release rate and cumulative dissolution percentage were determined according to the following conditions: USP dissolution test <711>, apparatus 2, 50 rpm, 500 ml (for 5 mg tablets) or 1000 ml (for 10 mg tablets) of 0.2% N, N-dimethyldodecylamine N-oxide (LDAO) or equivalent solvent, temperature 37° C.±0.5° C.

TABLE 1

| Strength | LIMS Date | Batch # | 16 h Diss (Q) % | Rel Rate (RR) %/h | n | Assay | Pct Fines % | Wt Gain mg/tab | Spray Time min. | Pan Wt kg |
|---|---|---|---|---|---|---|---|---|---|---|
| 10 mg | Sep. 22, 2005 | 3047431AR | 94.7 | 7.63 | 12 | 99.85 | 16.0 | 22.21 | 212.20 | 102.55 |
| 10 mg | Sep. 22, 2005 | 3047431CR | 92.8 | 7.39 | 12 | 99.55 | 16.0 | 21.73 | 212.34 | 102.59 |
| 10 mg | Sep. 22, 2005 | 3047431ER | 91.8 | 7.32 | 12 | 99.95 | 16.0 | 22.01 | 212.33 | 100.99 |
| 10 mg | Oct. 13, 2005 | 3047431RBX | 96.2 | 7.94 | 6 | 99.55 | 16.0 | 22.26 | 212.15 | 102.51 |
| 10 mg | Oct. 13, 2005 | 3047431RDX | 96.9 | 8.13 | 6 | 98.30 | 16.0 | 21.52 | 212.48 | 104.00 |
| 10 mg | Sep. 26, 2005 | 3047432BR | 97.1 | 8.04 | 12 | 99.60 | 18.0 | 21.12 | 212.35 | 106.00 |
| 10 mg | Oct. 17, 2005 | 3047432RAX | 97.7 | 7.92 | 6 | 99.00 | 18.0 | 20.87 | 211.94 | 103.30 |
| 10 mg | Oct. 17, 2005 | 3047432RCX | 99.7 | 8.3 | 6 | 98.80 | 18.0 | 21.35 | 212.27 | 104.63 |
| 10 mg | Oct. 17, 2005 | 3047432RDX | 98.5 | 8.21 | 6 | 99.25 | 18.0 | 21.20 | 212.44 | 104.65 |
| 10 mg | Oct. 17, 2005 | 3047432REX | 96.9 | 8 | 6 | 98.90 | 18.0 | 20.88 | 212.22 | 104.65 |
| 10 mg | Sep. 26, 2005 | 3047433DR | 94.8 | 7.71 | 12 | 98.50 | 18.0 | 21.68 | 212.18 | 103.88 |
| 10 mg | Oct. 20, 2005 | 3047433RAX | 94.8 | 7.42 | 6 | 99.05 | 18.0 | 21.48 | 212.21 | 104.10 |
| 10 mg | Oct. 20, 2005 | 3047433RBX | 93.7 | 7.52 | 6 | 98.75 | 18.0 | 21.70 | 212.40 | 103.97 |
| 10 mg | Oct. 20, 2005 | 3047433RCX | 95.1 | 7.81 | 6 | 98.15 | 18.0 | 21.50 | 212.29 | 104.14 |
| 10 mg | Oct. 21, 2005 | 3047433REX | 95.9 | 8.14 | 6 | 98.20 | 18.0 | 21.39 | 212.25 | 104.49 |
| 10 mg | Dec. 07, 2005 | 3048742A | 100.2 | 8.48 | 6 | 99.65 | 36.0 | 20.80 | 212.42 | 103.43 |
| 10 mg | Dec. 07, 2005 | 3048742B | 99.8 | 8.24 | 6 | 99.40 | 36.0 | 20.93 | 212.35 | 103.39 |
| 10 mg | Dec. 08, 2005 | 3048742C | 101.4 | 8.43 | 6 | 98.75 | 36.0 | 21.02 | 212.50 | 103.40 |
| 10 mg | Dec. 09, 2005 | 3048742D | 97.6 | 7.91 | 6 | 98.75 | 36.0 | 21.65 | 212.52 | 103.48 |
| 10 mg | Dec. 12, 2005 | 3048742E | 99.6 | 8.22 | 6 | 99.50 | 36.0 | 21.70 | 212.30 | 103.42 |
| 10 mg | Dec. 12, 2005 | 3048743A | 100.6 | 8.65 | 6 | 99.20 | 36.5 | 20.78 | 212.23 | 103.53 |
| 10 mg | Dec. 12, 2005 | 3048743B | 100.6 | 8.75 | 6 | 99.15 | 36.5 | 20.54 | 212.12 | 103.43 |
| 10 mg | Dec. 12, 2005 | 3048743C | 99.6 | 8.78 | 6 | 99.55 | 36.5 | 21.35 | 212.14 | 103.55 |
| 10 mg | Dec. 12, 2005 | 3048743D | 102 | 8.79 | 6 | 99.70 | 36.5 | 21.75 | 212.10 | 103.57 |
| 10 mg | Dec. 12, 2005 | 3048743E | 99.7 | 8.67 | 6 | 98.30 | 36.5 | 21.55 | 211.90 | 103.26 |
| 10 mg | Jan. 09, 2006 | 3048974A | 97.9 | 8.31 | 6 | 100.95 | 21.6 | 19.84 | 212.12 | 104.70 |
| 10 mg | Jan. 09, 2006 | 3048974B | 98.4 | 8.76 | 6 | 100.25 | 21.6 | 19.98 | 212.21 | 104.59 |
| 10 mg | Jan. 09, 2006 | 3048974C | 99.3 | 8.59 | 6 | 100.75 | 21.6 | 20.83 | 212.20 | 104.64 |
| 10 mg | Jan. 10, 2006 | 3048974D | 99.4 | 8.2 | 6 | 99.75 | 21.6 | 21.61 | 212.25 | 104.65 |
| 10 mg | Jan. 10, 2006 | 3048974E | 99.2 | 8.39 | 6 | 99.70 | 21.6 | 21.02 | 212.30 | 104.96 |
| 10 mg | Jan. 10, 2006 | 3049290A | 99.2 | 8.26 | 6 | 100.50 | 21.1 | 20.98 | 212.23 | 104.00 |
| 10 mg | Jan. 11, 2006 | 3049290B | 99.7 | 8.19 | 6 | 100.00 | 21.1 | 21.78 | 212.03 | 104.00 |
| 10 mg | Jan. 12, 2006 | 3049290C | 98.2 | 8.38 | 6 | 100.20 | 21.1 | 21.08 | 212.34 | 104.00 |
| 10 mg | Jan. 16, 2006 | 3049290D | 99.4 | 8.11 | 6 | 101.10 | 21.1 | 22.18 | 212.05 | 104.00 |
| 10 mg | Jan. 16, 2006 | 3049290E | 98.8 | 8.03 | 6 | 100.00 | 21.1 | 21.91 | 212.17 | 104.03 |
| 10 mg | Jan. 12, 2006 | 3049693XAX | 98.5 | 8.04 | 12 | 99.60 | 35.2 | 20.54 | 212.34 | 103.71 |
| 10 mg | Feb. 13, 2006 | 3049693XBX | 99.2 | 8.19 | 6 | 99.45 | 35.2 | 21.44 | 212.15 | 103.51 |
| 10 mg | Feb. 28, 2006 | 3049693XCX | 101.7 | 8.64 | 6 | 98.85 | 35.2 | 21.25 | 212.29 | 103.50 |
| 10 mg | Feb. 13, 2006 | 3049693XDX | 99 | 7.96 | 6 | 99.75 | 35.2 | 21.61 | 212.16 | 103.52 |
| 10 mg | Feb. 13, 2006 | 3049693XEX | 98.7 | 8.08 | 6 | 98.55 | 35.2 | 21.65 | 212.32 | 103.50 |
| 10 mg | Feb. 23, 2006 | 3049734XAX | 102.7 | 8.95 | 6 | 99.85 | 30.5 | 20.86 | 212.16 | 106.41 |
| 10 mg | Feb. 24, 2006 | 3049734XBX | 101 | 8.85 | 6 | 99.65 | 30.5 | 20.86 | 212.35 | 106.36 |
| 10 mg | Feb. 27, 2006 | 3049734XCX | 101.9 | 9.13 | 24 | 99.60 | 30.5 | 21.17 | 212.41 | 106.46 |
| 10 mg | Feb. 27, 2006 | 3049734XDX | 101 | 9.05 | 24 | 99.90 | 30.5 | 21.24 | 212.23 | 106.47 |
| 10 mg | Feb. 27, 2006 | 3049734XEX | 101.4 | 9.24 | 24 | 99.30 | 30.5 | 20.40 | 198.29 | 106.50 |
| 10 mg | May 24, 2006 | 3050790XAX | 95.1 | 8.31 | 12 | 96.30 | 17.8 | 21.39 | 198.25 | 104.00 |
| 10 mg | May 24, 2006 | 3050790XBX | 93.3 | 8.26 | 12 | 96.80 | 17.8 | 22.06 | 198.22 | 104.00 |
| 10 mg | May 24, 2006 | 3050790XCX | 94.1 | 8.49 | 12 | 96.40 | 17.8 | 22.10 | 198.29 | 104.00 |
| 10 mg | May 25, 2006 | 3050790XDX | 93.3 | 8.48 | 12 | 95.95 | 17.8 | 21.63 | 198.34 | 104.00 |
| 10 mg | May 25, 2006 | 3050790XEX | 89.8 | 7.57 | 12 | 95.55 | 17.8 | 21.75 | 198.11 | 104.00 |
| 10 mg | Jun. 15, 2006 | 3051213A | 102.7 | 9.43 | 24 | 97.65 | 28.1 | 20.52 | 198.50 | 104.00 |
| 10 mg | Jun. 15, 2006 | 3051213B | 101.5 | 8.95 | 12 | 97.80 | 28.1 | 21.27 | 198.20 | 104.00 |
| 10 mg | Jun. 21, 2006 | 3051213C | 100.8 | 8.89 | 6 | 100.85 | 28.1 | 21.72 | 198.50 | 104.00 |
| 10 mg | Jun. 15, 2006 | 3051213D | 101.3 | 9 | 12 | 98.05 | 28.1 | 21.32 | 198.20 | 104.00 |
| 10 mg | Jun. 15, 2006 | 3051213E | 100.6 | 8.94 | 12 | 99.05 | 28.1 | 21.26 | 198.39 | 104.00 |
| 10 mg | Jun. 23, 2006 | 3052176A | 92.4 | 8.35 | 6 | 99.40 | 13.0 | 20.61 | 198.17 | 104.00 |
| 10 mg | Jun. 23, 2006 | 3052176B | 92.7 | 8.41 | 6 | 100.05 | 13.0 | 20.47 | 198.39 | 104.00 |
| 10 mg | Jun. 26, 2006 | 3052176C | 95.3 | 8.84 | 12 | 99.75 | 13.0 | 20.44 | 198.27 | 104.00 |
| 10 mg | Jun. 26, 2006 | 3052176D | 94.6 | 8.93 | 24 | 99.15 | 13.0 | 20.76 | 198.30 | 104.00 |
| 10 mg | Jun. 27, 2006 | 3052176E | 92.9 | 8.19 | 6 | 98.95 | 13.0 | 21.04 | 198.17 | 104.00 |
| 10 mg | Jul. 05, 2006 | 3052314A | 96.5 | 8.25 | 6 | 99.90 | 25.0 | 21.37 | 198.29 | 103.90 |
| 10 mg | Jul. 11, 2006 | 3052314B | 100.4 | 8.88 | 6 | 99.50 | 25.0 | 20.59 | 198.10 | 103.91 |
| 10 mg | Jul. 11, 2006 | 3052314C | 99.4 | 8.34 | 6 | 99.55 | 25.0 | 21.91 | 198.39 | 103.90 |
| 10 mg | Jul. 11, 2006 | 3052314D | 102.2 | 8.6 | 6 | 99.35 | 25.0 | 22.06 | 198.25 | 103.86 |
| 10 mg | Jul. 11, 2006 | 3052314E | 98.9 | 8.47 | 6 | 97.65 | 25.0 | 21.79 | 198.31 | 103.93 |
| 5 mg | Dec. 15, 2004 | 3041648AR | 89.7 | 8.26 | 12 | 99.00 | 16.0 | 15.54 | 300.10 | 105.28 |
| 5 mg | Feb. 24, 2005 | 3041648BR | 96 | 8.55 | 12 | 101.50 | 16.0 | 16.06 | 304.81 | 105.26 |
| 5 mg | Jan. 24, 2005 | 3041648CR | 91.4 | 8.56 | 12 | 97.50 | 16.0 | 15.90 | 297.99 | 97.05 |
| 5 mg | Jan. 24, 2005 | 3041648ER | 88.9 | 8.29 | 12 | 97.60 | 16.0 | 15.61 | 312.05 | 108.03 |
| 5 mg | May 06, 2005 | 3041648RD | 84.7 | 7.78 | 12 | 97.85 | 16.0 | 15.83 | 309.65 | 105.20 |
| 5 mg | Jan. 28, 2005 | 3042050AR | 97.2 | 8.84 | 12 | 101.50 | 21.0 | 15.46 | 291.89 | 97.26 |
| 5 mg | Feb. 24, 2005 | 3042050BR | 92.6 | 8.27 | 12 | 101.20 | 21.0 | 16.10 | 307.74 | 101.37 |
| 5 mg | Jan. 26, 2005 | 3042050DR | 99.2 | 9.06 | 12 | 97.20 | 21.0 | 15.45 | 284.84 | 97.33 |
| 5 mg | May 09, 2005 | 3042050RC | 88.6 | 7.71 | 6 | 96.88 | 21.0 | 16.19 | 303.16 | 100.46 |
| 5 mg | Aug. 09, 2005 | 3042050REX | 93.5 | 8.6 | 12 | 97.05 | 21.0 | 16.39 | 277.90 | 89.86 |
| 5 mg | Jan. 27, 2005 | 3042051BR | 95 | 8.51 | 12 | 101.50 | 19.0 | 16.22 | 330.00 | 100.30 |

TABLE 1-continued

| Strength | LIMS Date | Batch # | 16 h Diss (Q) % | Rel Rate (RR) %/h | n | Assay | Pct Fines % | Wt Gain mg/tab | Spray Time min. | Pan Wt kg |
| --- | --- | --- | --- | --- | --- | --- | --- | --- | --- | --- |
| 5 mg | Feb. 26, 2005 | 3042051DR | 86.8 | 7.99 | 24 | 102.10 | 19.0 | 16.33 | 304.82 | 103.25 |
| 5 mg | Apr. 04, 2005 | 3042051RA | 90.9 | 8.22 | 6 | 99.30 | 19.0 | 16.46 | 293.45 | 98.76 |
| 5 mg | Apr. 04, 2005 | 3042051RC | 92.4 | 8.41 | 6 | 101.90 | 19.0 | 16.86 | 302.81 | 98.79 |
| 5 mg | Apr. 04, 2005 | 3042051RE | 89.3 | 8.03 | 6 | 99.70 | 19.0 | 16.39 | 303.75 | 100.30 |
| 5 mg | Apr. 25, 2005 | 3044646B | 86.9 | 7.88 | 6 | 98.75 | 17.0 | 16.26 | 303.12 | 105.61 |
| 5 mg | Apr. 25, 2005 | 3044646C | 84.7 | 7.62 | 12 | 99.35 | 17.0 | 16.14 | 303.10 | 105.52 |
| 5 mg | Apr. 25, 2005 | 3044646D | 84.7 | 7.67 | 12 | 99.30 | 17.0 | 16.25 | 302.99 | 105.62 |
| 5 mg | Apr. 25, 2005 | 3044646E | 84.4 | 7.61 | 24 | 99.15 | 17.0 | 16.07 | 303.77 | 105.67 |
| 5 mg | Apr. 07, 2005 | 3044647A | 83.6 | 7.41 | 24 | 96.80 | 19.0 | 16.07 | 303.53 | 104.25 |
| 5 mg | Apr. 07, 2005 | 3044647B | 88.1 | 7.88 | 6 | 98.00 | 19.0 | 16.31 | 303.40 | 104.13 |
| 5 mg | Apr. 11, 2005 | 3044647C | 83.8 | 7.69 | 12 | 97.90 | 19.0 | 16.49 | 303.21 | 104.24 |
| 5 mg | Apr. 11, 2005 | 3044647D | 83.7 | 7.47 | 12 | 98.25 | 19.0 | 15.98 | 303.25 | 104.10 |
| 5 mg | Apr. 11, 2005 | 3044647E | 82.9 | 8.15 | 24 | 97.65 | 19.0 | 15.90 | 303.22 | 105.81 |
| 5 mg | Apr. 12, 2005 | 3044669A | 85.6 | 7.57 | 6 | 98.40 | 18.0 | 16.51 | 304.35 | 104.30 |
| 5 mg | Apr. 18, 2005 | 3044669B | 89.8 | 8.19 | 6 | 98.65 | 18.0 | 16.36 | 303.06 | 104.24 |
| 5 mg | Apr. 18, 2005 | 3044669C | 87 | 7.75 | 6 | 99.05 | 18.0 | 16.59 | 303.14 | 104.40 |
| 5 mg | May 09, 2005 | 3044669D | 89.6 | 7.86 | 6 | 98.70 | 18.0 | 15.89 | 303.17 | 104.31 |
| 5 mg | Apr. 25, 2005 | 3044669E | 85.5 | 7.71 | 24 | 97.65 | 18.0 | 16.92 | 303.07 | 104.53 |
| 5 mg | May 16, 2005 | 3045325A | 80.3 | 7.39 | 24 | 96.60 | 13.0 | 16.19 | 303.47 | 101.87 |
| 5 mg | May 16, 2005 | 3045325B | 80.1 | 7.31 | 24 | 97.10 | 13.0 | 16.65 | 302.78 | 101.97 |
| 5 mg | May 25, 12005 | 3045325C | 80.2 | 7.33 | 24 | 96.00 | 13.0 | 17.02 | 302.99 | 101.96 |
| 5 mg | May 16, 2005 | 3045325D | 80.6 | 7.41 | 24 | 97.65 | 13.0 | 16.49 | 298.95 | 102.03 |
| 5 mg | May 16, 2005 | 3045325E | 79.8 | 7.22 | 24 | 98.15 | 13.0 | 16.36 | 302.20 | 101.92 |
| 5 mg | May 25, 2005 | 3045326A | 89.2 | 7.99 | 12 | 99.35 | 22.0 | 16.00 | 303.11 | 105.44 |
| 5 mg | May 25, 2005 | 3045326B | 88.9 | 8.08 | 6 | 100.60 | 22.0 | 16.14 | 303.10 | 105.37 |
| 5 mg | May 31, 2005 | 3045326E | 88 | 7.99 | 12 | 99.30 | 22.0 | 16.12 | 303.08 | 105.37 |
| 5 mg | May 31, 2005 | 3045327A | 86.6 | 7.8 | 6 | 99.20 | 17.0 | 15.79 | 303.54 | 105.13 |
| 5 mg | May 31, 2005 | 3045327B | 89.8 | 8.38 | 6 | 99.00 | 17.0 | 15.79 | 303.08 | 105.19 |
| 5 mg | Jun. 06, 2005 | 3045327C | 87.4 | 7.76 | 6 | 98.20 | 17.0 | 16.36 | 303.14 | 105.09 |
| 5 mg | Jun. 06, 2005 | 3045327D | 85.7 | 7.86 | 6 | 98.00 | 17.0 | 16.02 | 303.37 | 105.17 |
| 5 mg | Jun. 06, 2005 | 3045327E | 84.2 | 7.48 | 12 | 97.35 | 17.0 | 15.95 | 303.03 | 105.17 |
| 5 mg | Jun. 13, 2005 | 3045328A | 85.4 | 7.8 | 24 | 97.85 | 17.0 | 15.81 | 303.20 | 105.57 |
| 5 mg | Jun. 16, 2005 | 3045328B | 86.2 | 7.75 | 12 | 98.30 | 17.0 | 15.80 | 303.05 | 105.52 |
| 5 mg | Jun. 16, 2005 | 3045328C | 90.2 | 8.14 | 6 | 97.00 | 17.0 | 16.05 | 303.32 | 105.55 |
| 5 mg | Jun. 16, 2005 | 3045328D | 83.9 | 7.56 | 12 | 97.70 | 17.0 | 16.12 | 303.05 | 105.66 |
| 5 mg | Jun. 17, 2005 | 3045328E | 83.3 | 7.29 | 12 | 96.55 | 17.0 | 16.19 | 303.15 | 105.55 |
| 5 mg | Jun. 20, 2005 | 3045329A | 84.1 | 7.68 | 12 | 97.25 | 13.0 | 15.69 | 303.07 | 105.15 |
| 5 mg | Jun. 20, 2005 | 3045329B | 83.3 | 7.66 | 12 | 98.05 | 13.0 | 16.26 | 303.14 | 105.18 |
| 5 mg | Jun. 23, 2005 | 3045329C | 82.9 | 7.51 | 24 | 96.80 | 13.0 | 15.99 | 303.07 | 105.13 |
| 5 mg | Jun. 23, 2005 | 3045329D | 83.6 | 7.6 | 24 | 97.50 | 13.0 | 16.26 | 303.14 | 105.07 |
| 5 mg | Jun. 24, 2005 | 3045329E | 85 | 7.79 | 12 | 98.60 | 13.0 | 16.20 | 303.05 | 105.14 |
| 5 mg | Aug. 04, 2005 | 3045330C | 89.1 | 7.97 | 6 | 99.50 | 13.0 | 16.38 | 303.36 | 100.33 |
| 5 mg | Aug. 04, 2005 | 3045330D | 85.6 | 7.57 | 24 | 99.75 | 13.0 | 16.22 | 303.39 | 100.26 |
| 5 mg | Aug. 05, 2005 | 3045330E | 84.7 | 7.58 | 12 | 98.40 | 13.0 | 16.68 | 303.39 | 100.29 |
| 5 mg | Dec. 19, 2005 | 3046533A | 92.2 | 8.59 | 6 | 99.15 | 36.0 | 15.46 | 303.16 | 104.45 |
| 5 mg | Nov. 18, 2005 | 3046533B | 96.3 | 8.95 | 6 | 98.25 | 36.0 | 14.84 | 303.42 | 104.39 |
| 5 mg | Jan. 09, 2006 | 3046533C | 95.9 | 8.99 | 6 | 99.50 | 36.0 | 16.14 | 303.09 | 104.51 |
| 5 mg | Jan. 16, 2006 | 3046533D | 96.7 | 8.79 | 6 | 99.35 | 36.0 | 15.57 | 303.08 | 104.40 |
| 5 mg | Jan. 09, 2006 | 3046533E | 95 | 8.81 | 6 | 98.95 | 36.0 | 14.99 | 303.33 | 104.56 |
| 5 mg | Jan. 09, 2006 | 3046534A | 98 | 8.88 | 6 | 99.85 | 37.0 | 14.69 | 303.05 | 105.23 |
| 5 mg | Apr. 13, 2006 | 3046534B | 92.6 | 8.45 | 6 | 97.33 | 37.0 | 16.19 | 312.34 | 105.30 |
| 5 mg | Apr. 14, 2006 | 3046534C | 94.8 | 8.45 | 6 | 97.00 | 37.0 | 15.34 | 312.25 | 105.29 |
| 5 mg | Mar. 20, 2006 | 3046534D | 94.1 | 8.56 | 6 | 97.20 | 37.0 | 15.53 | 312.08 | 105.40 |
| 5 mg | Mar. 20, 2006 | 3046534E | 92.2 | 8.31 | 6 | 97.00 | 37.0 | 16.08 | 315.54 | 102.81 |
| 5 mg | Nov. 21, 2005 | 3047964AR | 97.1 | 8.58 | 12 | 98.25 | 36.0 | 15.56 | 303.13 | 99.71 |
| 5 mg | Jan. 03, 2006 | 3047964RBX | 97.5 | 8.43 | 6 | 98.55 | 36.0 | 16.32 | 303.45 | 99.64 |
| 5 mg | Jan. 03, 2006 | 3047964RCX | 96.5 | 8.47 | 6 | 99.05 | 36.0 | 16.20 | 303.13 | 99.83 |
| 5 mg | Jan. 03, 2006 | 3047964RDX | 95.1 | 8.57 | 6 | 99.00 | 36.0 | 16.16 | 303.33 | 99.87 |
| 5 mg | Jan. 03, 2006 | 3047964REX | 92.9 | 8.34 | 6 | 97.50 | 36.0 | 16.67 | 303.33 | 99.83 |
| 5 mg | Feb. 03, 2006 | 3049171A | 92.6 | 8.18 | 6 | 100.05 | 29.0 | 16.15 | 303.11 | 103.56 |
| 5 mg | Feb. 06, 2006 | 3049171B | 93.3 | 8.11 | 6 | 99.60 | 29.0 | 16.21 | 303.10 | 103.50 |
| 5 mg | Feb. 06, 2006 | 3049171C | 91 | 8.12 | 6 | 99.70 | 29.0 | 16.23 | 303.28 | 103.48 |
| 5 mg | Feb. 06, 2006 | 3049171D | 89.1 | 7.69 | 6 | 100.10 | 29.0 | 15.87 | 303.03 | 103.49 |
| 5 mg | Feb. 06, 2006 | 3049171E | 89.8 | 7.93 | 6 | 100.15 | 29.0 | 15.81 | 303.10 | 103.50 |
| 5 mg | Mar. 20, 2006 | 3049347A | 95.4 | 8.24 | 6 | 98.00 | 32.0 | 15.58 | 312.20 | 102.37 |
| 5 mg | Mar. 20, 2006 | 3049347B | 96.9 | 8.53 | 6 | 98.50 | 32.0 | 16.36 | 312.20 | 102.40 |
| 5 mg | Mar. 21, 2006 | 3049347C | 96.8 | 8.35 | 6 | 99.05 | 32.0 | 16.57 | 312.12 | 102.46 |
| 5 mg | Mar. 21, 2006 | 3049347D | 98.7 | 8.25 | 6 | 99.30 | 32.0 | 15.67 | 312.27 | 102.44 |

TABLE 1-continued

| Strength | LIMS Date | Batch # | 16 h Diss (Q) % | Rel Rate (RR) %/h | n | Assay | Pct Fines % | Wt Gain mg/tab | Spray Time min. | Pan Wt kg |
|---|---|---|---|---|---|---|---|---|---|---|
| 5 mg | Mar. 22, 2006 | 3049347E | 95.6 | 8.17 | 6 | 98.65 | 32.0 | 16.55 | 312.24 | 102.50 |
| 5 mg | Apr. 03, 2006 | 3050452A | 91.2 | 8.29 | 6 | 95.65 | 27.0 | 16.32 | 312.20 | 103.33 |
| 5 mg | Apr. 04, 2006 | 3050452B | 89.3 | 7.98 | 6 | 96.08 | 27.0 | 15.80 | 312.19 | 103.30 |
| 5 mg | Mar. 30, 2006 | 3050452C | 88.2 | 7.94 | 6 | 94.29 | 27.0 | 16.29 | 312.51 | 103.37 |
| 5 mg | Mar. 31, 2006 | 3050452D | 88 | 8 | 6 | 96.70 | 27.0 | 15.87 | 312.06 | 103.37 |
| 5 mg | Apr. 03, 2006 | 3050452E | 87.8 | 7.94 | 6 | 94.75 | 27.0 | 16.14 | 312.10 | 103.30 |
| 5 mg | Apr. 05, 2006 | 3050453A | 91.8 | 8.19 | 6 | 100.65 | 31.0 | 16.55 | 312.29 | 106.30 |
| 5 mg | Apr. 12, 2006 | 3050453B | 92 | 8.23 | 6 | 99.25 | 31.0 | 16.01 | 312.04 | 106.30 |
| 5 mg | Apr. 17, 2006 | 3050453C | 93 | 8.34 | 6 | 99.60 | 31.0 | 15.99 | 312.62 | 106.30 |
| 5 mg | Apr. 06, 2006 | 3050453D | 91.6 | 8.12 | 6 | 99.20 | 31.0 | 15.68 | 312.75 | 106.31 |
| 5 mg | Apr. 20, 2006 | 3050453E | 92.3 | 8.29 | 6 | 98.55 | 31.0 | 16.03 | 312.43 | 106.30 |
| 5 mg | Apr. 20, 2006 | 3051282A | 88 | 7.7 | 12 | 98.65 | 29.0 | 16.45 | 312.35 | 103.48 |
| 5 mg | Apr. 24, 2006 | 3051282B | 88 | 7.89 | 6 | 97.95 | 29.0 | 16.43 | 312.23 | 103.50 |
| 5 mg | Apr. 24, 2006 | 3051282C | 87.7 | 7.75 | 6 | 98.35 | 29.0 | 16.45 | 312.41 | 103.50 |
| 5 mg | Apr. 24, 2006 | 3051282D | 86.1 | 7.61 | 6 | 98.25 | 29.0 | 16.41 | 312.35 | 103.50 |
| 5 mg | May 11, 2006 | 3051282E | 90.6 | 8.13 | 6 | 96.90 | 29.0 | 15.91 | 312.73 | 103.50 |
| 5 mg | May 11, 2006 | 3051674A | 89.9 | 7.85 | 6 | 98.65 | 30.0 | 16.24 | 312.37 | 104.28 |
| 5 mg | May 12, 2006 | 3051674B | 90.7 | 8.07 | 6 | 98.40 | 30.0 | 16.60 | 312.20 | 104.30 |
| 5 mg | May 15, 2006 | 3051674C | 91.9 | 8.18 | 6 | 98.85 | 30.0 | 16.87 | 312.21 | 104.27 |
| 5 mg | May 15, 2006 | 3051674D | 91.1 | 7.8 | 6 | 99.20 | 30.0 | 15.87 | 312.14 | 104.30 |
| 5 mg | May 15, 2006 | 3051674E | 88.1 | 7.56 | 6 | 99.00 | 30.0 | 16.26 | 312.38 | 102.32 |
| 5 mg | Jun. 22, 2006 | 3051681A | 82.6 | 7.4 | 24 | 97.25 | 18.0 | 17.52 | 312.13 | 100.18 |
| 5 mg | Jul. 18, 2006 | 3051681C | 87.7 | 7.85 | 6 | 96.18 | 18.0 | 17.06 | 312.32 | 100.10 |
| 5 mg | Jul. 18, 2006 | 3051681D | 83.3 | 7.37 | 12 | 97.45 | 18.0 | 17.43 | 312.12 | 100.90 |
| 5 mg | Jul. 18, 2006 | 3051681E | 83 | 7.45 | 12 | * | 18.0 | 17.19 | 312.18 | 100.11 |
| 5 mg | Jun. 27, 2006 | 3051682A | 81.2 | 7.32 | 24 | 99.60 | 14.0 | 16.77 | 312.26 | 103.67 |
| 5 mg | Jun. 28, 2006 | 3051682B | 81.5 | 7.29 | 24 | 99.85 | 14.0 | 16.92 | 312.28 | 103.67 |
| 5 mg | Jun. 29, 2006 | 3051682C | 83.9 | 7.75 | 12 | 98.75 | 14.0 | 16.97 | 312.29 | 103.67 |
| 5 mg | Jun. 30, 2006 | 3051682D | 79.5 | 7.19 | 24 | 100.00 | 14.0 | 17.13 | 312.41 | 103.70 |
| 5 mg | Jun. 30, 2006 | 3051682E | 76.9 | 7.02 | 24 | 98.95 | 14.0 | 17.31 | 312.05 | 103.70 |

An exemplary table derived through an application of the LOESS model to the historical data in table 1 with the goal of obtaining a release rate of 8.03%/h is shown below in Table 2 for 5 mg isradipine controlled release tablets and Table 3 for 10 mg isradipine tablets.

TABLE 2

| Target Wt Gain (mg/tab) | Pan wts (kg) | | | | | | | | | | | | | | |
|---|---|---|---|---|---|---|---|---|---|---|---|---|---|---|---|
| Pct fines (%) | 99.0 | 99.5 | 100.0 | 100.5 | 101.0 | 101.5 | 102.0 | 102.5 | 103.0 | 103.5 | 104.0 | 104.5 | 105.0 | 105.5 | 106.0 |
| 13 | 16.2 | 16.2 | 16.1 | 16.0 | 15.9 | 15.8 | 15.7 | 15.6 | 15.5 | | | | | | |
| 14 | 16.3 | 16.2 | 16.2 | 16.1 | 16.0 | 15.9 | 15.8 | 15.7 | 15.6 | 15.5 | | | | | |
| 15 | 16.4 | 16.3 | 16.2 | 16.1 | 16.1 | 16.0 | 15.9 | 15.7 | 15.7 | 15.6 | 15.5 | 15.5 | | | |
| 16 | 16.4 | 16.3 | 16.3 | 16.2 | 16.1 | 16.0 | 16.0 | 15.8 | 15.7 | 15.7 | 15.6 | 15.5 | 15.5 | 15.5 | |
| 17 | 16.5 | 16.4 | 16.3 | 16.2 | 16.2 | 16.1 | 16.0 | 15.8 | 15.8 | 15.7 | 15.6 | 15.6 | 15.5 | 15.5 | 15.5 |
| 18 | 16.5 | 16.5 | 16.4 | 16.3 | 16.2 | 16.2 | 16.1 | 15.9 | 15.8 | 15.8 | 15.7 | 15.6 | 15.6 | 15.6 | 15.5 |
| 19 | 16.6 | 16.5 | 16.4 | 16.4 | 16.3 | 16.2 | 16.2 | 16.0 | 15.9 | 15.8 | 15.7 | 15.7 | 15.7 | 15.6 | 15.6 |
| 20 | 16.6 | 16.6 | 16.5 | 16.4 | 16.3 | 16.3 | 16.2 | 16.0 | 16.0 | 15.9 | 15.8 | 15.8 | 15.7 | 15.7 | 15.6 |
| 21 | 16.7 | 16.6 | 16.5 | 16.5 | 16.4 | 16.3 | 16.3 | 16.1 | 16.0 | 16.0 | 15.9 | 15.8 | 15.8 | 15.7 | 15.7 |
| 22 | 16.8 | 16.7 | 16.6 | 16.5 | 16.5 | 16.4 | 16.3 | 16.1 | 16.1 | 16.0 | 15.9 | 15.9 | 15.8 | 15.8 | 15.7 |
| 23 | 16.8 | 16.7 | 16.7 | 16.6 | 16.5 | 16.5 | 16.4 | 16.2 | 16.1 | 16.1 | 16.0 | 15.9 | 15.9 | 15.9 | 15.8 |
| 24 | 16.9 | 16.8 | 16.7 | 16.7 | 16.6 | 16.5 | 16.5 | 16.2 | 16.2 | 16.1 | 16.1 | 16.0 | 16.0 | 15.9 | 15.9 |
| 25 | 16.9 | 16.9 | 16.8 | 16.7 | 16.7 | 16.6 | 16.5 | 16.3 | 16.2 | 16.2 | 16.1 | 16.1 | 16.0 | 16.0 | 15.9 |
| 26 | 17.0 | 16.9 | 16.8 | 16.8 | 16.7 | 16.6 | 16.6 | 16.4 | 16.3 | 16.3 | 16.2 | 16.2 | 16.1 | 16.1 | 16.0 |
| 27 | 17.0 | 17.0 | 16.9 | 16.8 | 16.8 | 16.7 | 16.7 | 16.5 | 16.4 | 16.3 | 16.3 | 16.2 | 16.2 | 16.1 | 16.1 |
| 28 | 17.0 | 17.0 | 17.0 | 16.9 | 16.9 | 16.8 | 16.7 | 16.5 | 16.5 | 16.4 | 16.4 | 16.3 | 16.3 | 16.2 | 16.2 |
| 29 | 17.0 | 17.0 | 17.0 | 17.0 | 16.9 | 16.9 | 16.8 | 16.6 | 16.6 | 16.5 | 16.5 | 16.4 | 16.4 | 16.3 | 16.3 |
| 30 | 17.0 | 17.0 | 17.0 | 17.0 | 17.0 | 16.9 | 16.9 | 16.7 | 16.6 | 16.6 | 16.5 | 16.5 | 16.4 | 16.4 | 16.3 |
| 31 | 17.0 | 17.0 | 17.0 | 17.0 | 17.0 | 16.9 | 16.9 | 16.8 | 16.7 | 16.7 | 16.6 | 16.6 | 16.5 | 16.5 | 16.4 |
| 32 | 17.0 | 17.0 | 17.0 | 17.0 | 17.0 | 17.0 | 16.9 | 16.8 | 16.8 | 16.7 | 16.7 | 16.6 | 16.6 | 16.5 |
| 33 | 17.0 | 17.0 | 17.0 | 17.0 | 17.0 | 17.0 | 17.0 | 16.9 | 16.8 | 16.8 | 16.8 | 16.7 | 16.7 | 16.6 |
| 34 | 17.0 | 17.0 | 17.0 | 17.0 | 17.0 | 17.0 | 17.0 | 17.0 | 16.9 | 16.9 | 16.9 | 16.8 | 16.8 | 16.7 |
| 35 | 17.0 | 17.0 | 17.0 | 17.0 | 17.0 | 17.0 | 17.0 | 17.0 | 17.0 | 17.0 | 17.0 | 16.9 | 16.9 | 16.8 |
| 36 | 17.0 | 17.0 | 17.0 | 17.0 | 17.0 | 17.0 | 17.0 | 17.0 | 17.0 | 17.0 | 17.0 | 17.0 | 16.9 | 16.9 |

TABLE 3

| Target Wt Gain (mg/tab) | | | | Pan wts (kg) | | | | |
|---|---|---|---|---|---|---|---|---|
| Pct fines (%) | 102.5 | 103.0 | 103.5 | 104.0 | 104.5 | 105.0 | 105.5 | 106.0 |
| 13 | 20.7 | 21.3 | 21.6 | 21.2 | 21.4 | 21.2 | 20.9 | 20.6 |
| 14 | 20.8 | 21.3 | 21.7 | 21.3 | 21.5 | 21.3 | 21.1 | 20.8 |
| 15 | 20.8 | 21.3 | 21.7 | 21.4 | 21.7 | 21.5 | 21.3 | 21.1 |
| 16 | 20.9 | 21.4 | 21.8 | 21.6 | 21.9 | 21.7 | 21.6 | 21.4 |
| 17 | 20.9 | 21.4 | 21.8 | 21.8 | 22.1 | 22.0 | 21.8 | 21.7 |
| 18 | 20.9 | 21.5 | 21.9 | 22.1 | 22.1 | 22.1 | 22.1 | 22.0 |
| 19 | 21.0 | 21.5 | 22.0 | 22.1 | 22.1 | 22.1 | 22.1 | 22.1 |
| 20 | 21.1 | 21.6 | 22.0 | 22.1 | 22.1 | 22.1 | 22.1 | |
| 21 | 21.1 | 21.7 | 22.1 | 22.1 | 22.1 | 22.1 | | |
| 22 | 21.2 | 21.7 | 22.1 | 22.1 | | | | |
| 23 | 21.2 | 21.8 | 22.1 | 22.1 | | | | |
| 24 | 21.3 | 21.9 | 22.1 | | | | | |
| 25 | 21.4 | 22.0 | 22.1 | | | | | |
| 26 | 21.5 | 22.1 | 22.1 | | | | | |
| 27 | 21.6 | 22.1 | 22.1 | | | | | |
| 28 | 21.7 | 22.1 | 22.1 | | | | | |
| 29 | 21.8 | 22.1 | 22.1 | | | | | |
| 30 | 22.0 | 22.1 | 22.1 | | | | | |
| 31 | 22.1 | 22.1 | 22.1 | | | | | |
| 32 | 22.1 | 22.1 | 22.1 | | | | | |
| 33 | 22.1 | 22.1 | 22.1 | | | | | |
| 34 | 22.1 | 22.1 | | | | | | |
| 35 | 22.1 | 22.1 | | | | | | |
| 36 | 22.1 | 22.1 | | | | | | |

Tables 4 and 5 show the results of an embodiment using a LOESS model with a goal of a release rate (RR) of 8.03%/hr. Table 4 shows the results for 5 mg controlled release tablets. Table 5 shows the results for 10 mg controlled release tablets. In these tables, N is the number of tablets for which the dissolution and release rate were tested. Q is the cumulative dissolution at 16 hours, a percentage of which is shown for the controlled release tablets at 4 hours (4 hr), 8 hours (8 hr), 12 hours, (12 hr), and 16 hours (16 hr). RR is the release rate shown in percentage/hour.

TABLE 4

5 mg batches with the use of a LOESS Model

| Batch # | N | 4 hr | 8 hr | 12 hr | Q % 16 hr | RR %/hr | Wt. Gain (mg) | Spray Time (min) | Pan Load (kg) |
|---|---|---|---|---|---|---|---|---|---|
| 3053603EX | 24 | 21 | 54.4 | 78.9 | 82.8 | 7.24 | 15.15 | 296.84 | 104.86 |
| 3053884EX | 12 | 22.3 | 57.3 | 84.8 | 88.9 | 7.81 | 16.21 | 291.88 | 102.0 |
| 3053487EX | 12 | 22 | 57.2 | 84.4 | 89.3 | 7.8 | 16.86 | 311.82 | 99.0 |

TABLE 5

10 mg batches with the use of a LOESS Model

| Batch # | N | 4 hr | 8 hr | 12 hr | Q % 16 hr | RR %/hr | Wt. Gain (mg) | Spray Time (min) | Pan Load (kg) |
|---|---|---|---|---|---|---|---|---|---|
| 3052815EX | 12 | 17.5 | 49.8 | 81.9 | 97.9 | 8.05 | 21.79 | 222.73 | 103.96 |
| 3054416EX | 12 | 17.2 | 49.4 | 81.7 | 95.6 | 8.06 | 21.34 | 206.56 | 102.5 |
| 3053587EX | 12 | 18.2 | 51.3 | 84.9 | 97.2 | 8.34 | 21.69 | 208.03 | 103 |

Figure 2:
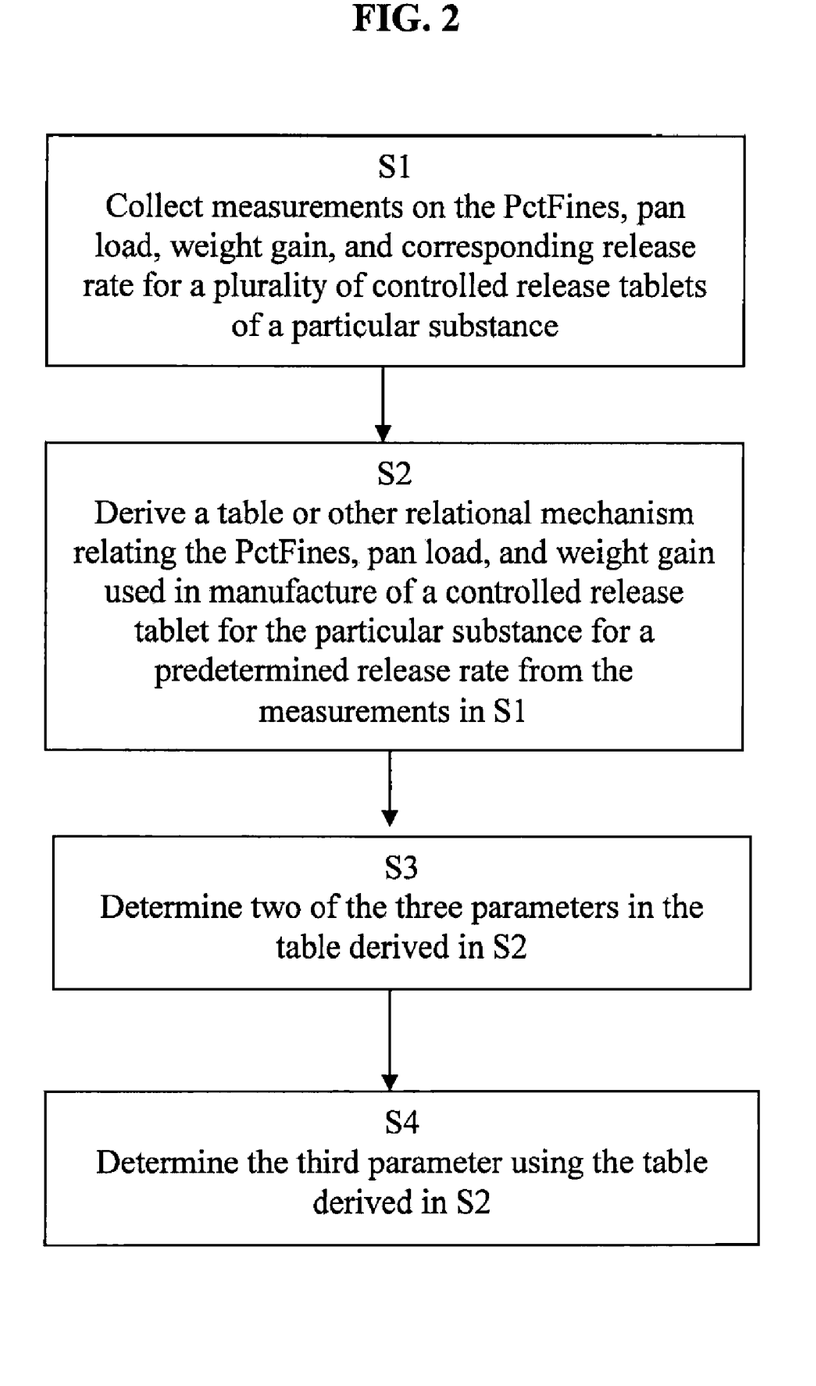
FIG. 2 shows a flow diagram of an exemplary embodiment of a method applying the present invention.

FIG. 2 shows a flow diagram of the steps involved in an exemplary embodiment of the present invention. In step S1 measurements are collected on at least PctFines, pan load, membrane weight gain, and the corresponding release rate for a plurality of batches of controlled release tablets having a particular active substance. In step S2 a table for a predetermined release rate is derived from the measurements in S1, for example, using one of multiple linear regression, a neural network, local regression, such as a LOESS model, or Monte Carlo simulation. The table shows the combinations of Pct-Fines, pan load, and weight gain that will produce the predetermined release rate. In step S3, two of the parameters in the table derived in step S2 are selected. These parameters will be applied in the manufacture of the controlled release tablet. In step S4, the third parameter is determined using the table derived in step S2 and the parameters selected in step S3. The third parameter will then be applied in the manufacturing process of the controlled release tablet in order to produce a tablet having the predetermined release rate.

Although each of the embodiments above have been described as being applied to a tablet, the present invention is not limited in application to a controlled release tablet. The present invention can also be used in the manufacture of a controlled release pellet or capsule, for example.

Figure 3:
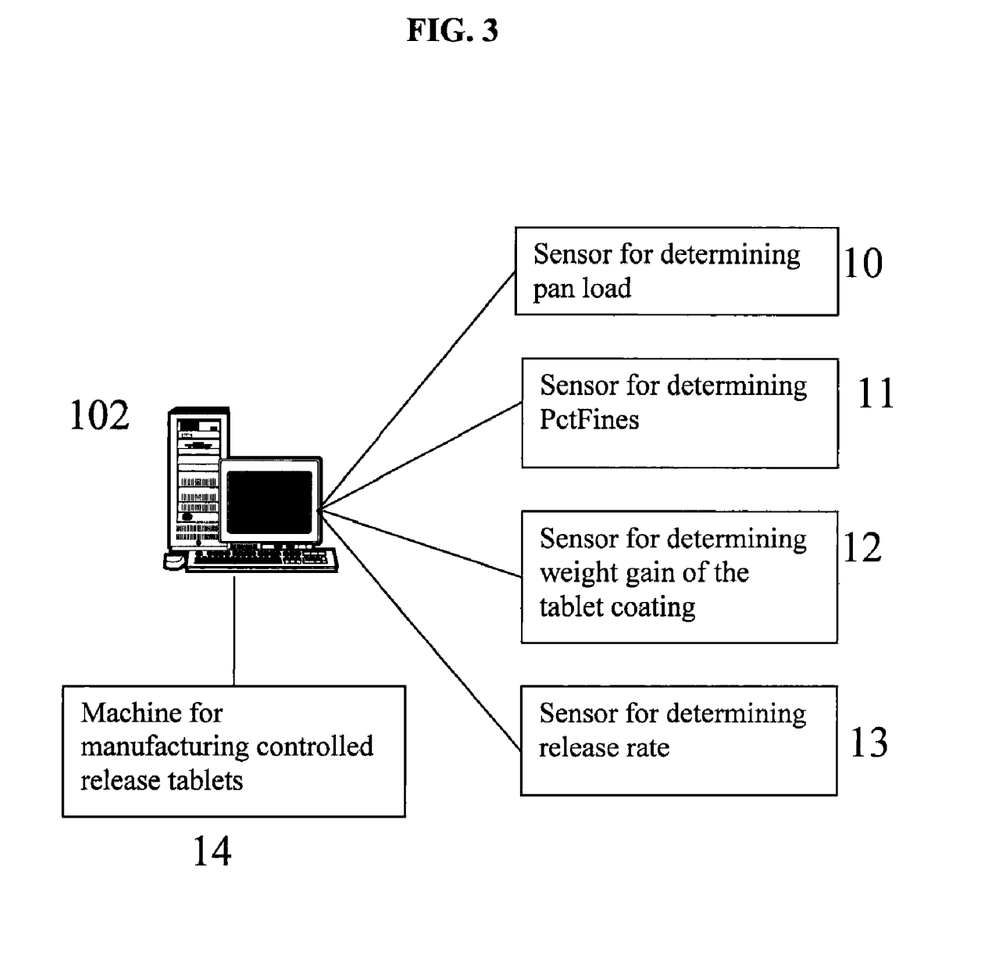
FIG. 3 shows a diagram of various features of an example computer system for use in conjunction with an embodiment of the present invention.

FIG. 3 shows various features of an example computer system for use in conjunction with an embodiment of the present invention. The computer system is used by a user to access data, store data measurements, derive tables, make calculations, control the parameters of manufacturing, and perform other steps in accordance with methods of the present invention, such as by using software and other computer features. The terminal 102 may comprise, for example, a personal computer (PC), minicomputer, mainframe computer, or microcomputer or other device having a processor and a repository for data or that is capable of accessing a repository of data. The terminal is connected to a sensor for determining the pan load 10, a sensor for determining the percentage fines 11, and a sensor for determining the weight gain of the tablet coating 12. These sensors may be coupled to the terminal with, for example, wired, wireless, or fiberoptic links. Sensors 10, 11, 12 and 13, measure the PctFines, pan load, weight gain, and release rate used in manufacturing controlled release tablets. These measurements may also be made manually or by any other method. The measurements may then be input into the terminal. Measurements of these parameters are obtained for a plurality of batches of controlled release tablets of a particular substance. The measurement information can be used to derive a table or other relational mechanism relating the PctFines, pan load, and weight gain used in the manufacture of a controlled release tablet for the particular substance for a predetermined release rate using a mathematical model, such as multiple linear regression, a neural network, local regression, such as a LOESS model, or Monte Carlo simulation.

In one embodiment according to the present invention, the terminal 102 is coupled to at least one machine 14 used in manufacturing controlled release tablets. In manufacturing controlled release tablets using the same active substance and for which the predetermined release rate is desired, the terminal 102 uses the derived table and at least one sensor to coordinate the manufacturing parameters of pan load, weight gain, and PctFines in order to achieve the desired release rate.

As discussed above, once the table is defined, if two of three influencing parameters are predetermined and held constant, the third parameter can be selected during manufacture of the controlled release tablet to ensure the optimal release rate. Similarly, if one parameter is constant and a second parameter varies, the third parameter may be varied so as to maintain the optimal release rate of the manufactured controlled release tablets.

Figure 4:
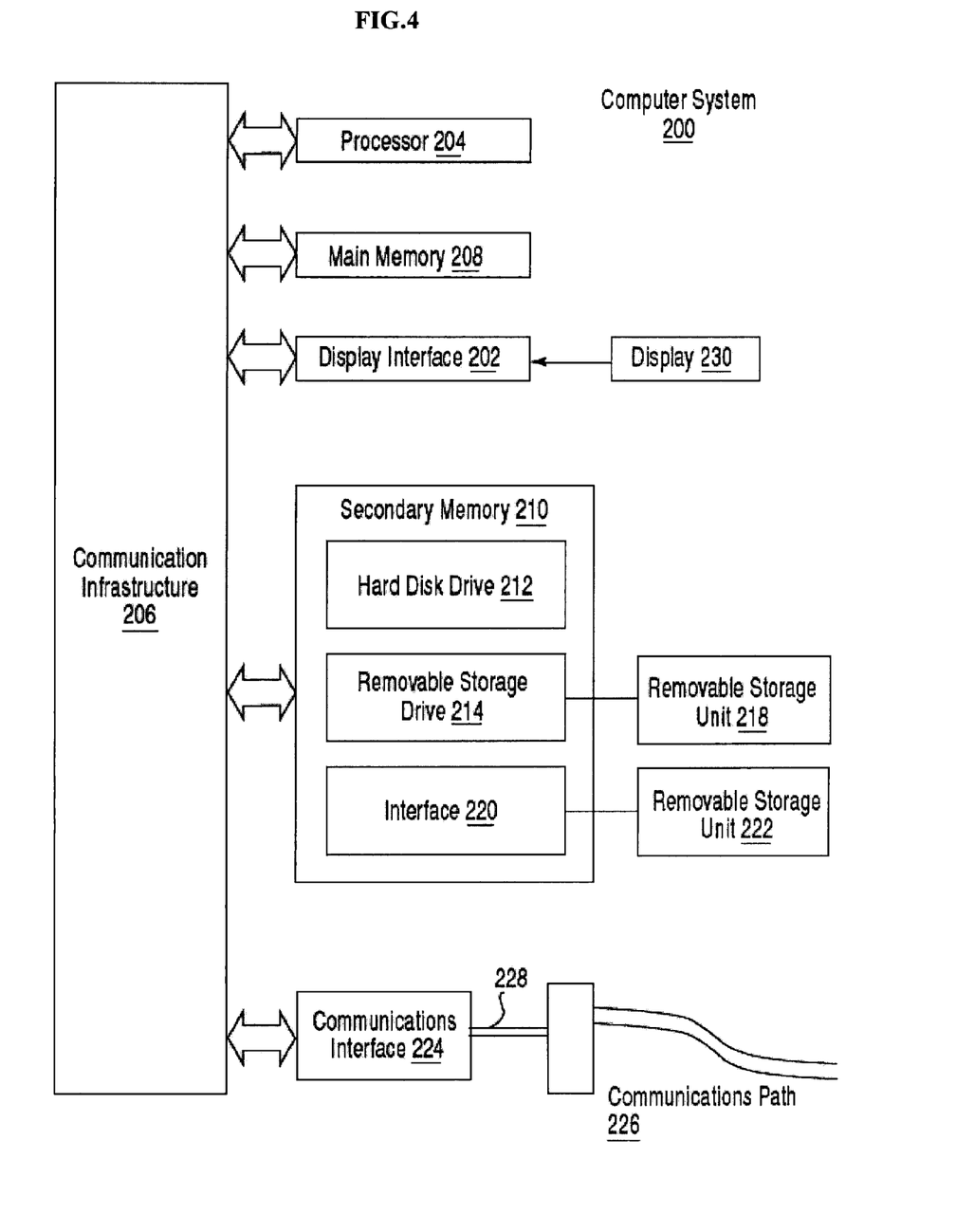
FIG. 4 shows an exemplary system diagram of various hardware components and other features, in accordance with an embodiment of the present invention.

The present invention may be implemented using hardware, software or a combination thereof and may be implemented in one or more computer systems or other processing systems. In one embodiment, the invention is directed toward one or more computer systems capable of carrying out the functionality described herein. An example of such a computer system 200 is shown in FIG. 4.

Computer system 200 includes one or more processors, such as processor 204. The processor 204 is connected to a communication infrastructure 206 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 200 can include a display interface 202 that forwards graphics, text, and other data from the communication infrastructure 206 (or from a frame buffer not shown) for display on the display unit 230. Computer system 200 also includes a main memory 208, preferably random access memory (RAM), and may also include a secondary memory 210. The secondary memory 210 may include, for example, a hard disk drive 212 and/or a removable storage drive 214, representing a floppy disk drive, a magnetic tape drive, an optical disk drive, etc. The removable storage drive 214 reads from and/or writes to a removable storage unit 218 in a well-known manner. Removable storage unit 218, represents a floppy disk, magnetic tape, optical disk, etc., which is read by and written to removable storage drive 214. As will be appreciated, the removable storage unit 218 includes a computer usable storage medium having stored therein computer software and/or data.

In alternative embodiments, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as that found in video game devices), a removable memory chip (such as an erasable programmable read only memory (EPROM), or programmable read only memory (PROM)) and associated socket, and other removable storage units 222 and interfaces 220, which allow software and data to be transferred from the removable storage unit 222 to computer system 200.

Computer system 200 may also include a communications interface 224. Communications interface 224 allows software and data to be transferred between computer system 200 and external devices. Examples of communications interface 224 may include a modem, a network interface (such as an Ethernet card), a communications port, a Personal Computer Memory Card International Association (PCMCIA) slot and card, etc. Software and data transferred via communications interface 224 are in the form of signals 228, which may be electronic, electromagnetic, optical or other signals capable of being received by communications interface 224. These signals 228 are provided to communications interface 224 via a communications path (e.g., channel) 226. This path 226 carries signals 228 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 214, a hard disk installed in hard disk drive 212, and signals 228. These computer program products provide software to the computer system 200. The invention is directed to such computer program products.

Computer programs (also referred to as computer control logic) are stored in main memory 208 and/or secondary memory 210. Computer programs may also be received via communications interface 224. Such computer programs, when executed, enable the computer system 200 to perform the features of the present invention, as discussed herein. In particular, the computer programs, when executed, enable the processor 204 to perform the features of the present invention. Accordingly, such computer programs represent controllers of the computer system 200.

In an embodiment where the invention is implemented using software, the software may be stored in a computer program product and loaded into computer system 200 using removable storage drive 214, hard drive 212, or communications interface 224. The control logic (software), when executed by the processor 204, causes the processor 204 to perform the functions of the invention as described herein. In another embodiment, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

ILLUSTRATIVE APPLICATION

In an exemplary embodiment, the active substance is isradipine, the coating layer is a cellulose acetate membrane, and the tablet strength is either 5 mg or 10 mg. In this embodiment, the predetermined approved release rate range is 7.03%/h to 9.02%/h. The optimal release rate is within this predetermined range, or more preferred near the center of the range. One optimal release rate is about 8.03%/h. Using the data in Table 1, Table 2 and Table 3 are derived using local regression such as a LOESS modeling method. This LOESS model method may be implemented, for example, using SAS 9.1 software, made by SAS Institute of Cary, N.C. The tables may also be derived by other modeling methods, such as by the use of a neural network or Monte Carlo simulation. The neural network may be implemented, for example, using JMP 6.0 software, made by SAS Institute of Cary, N.C. Any similar modeling method may be used to derive the tables. In Table 2 and Table 3, the values for the PctFines, pan load, and weight gain were limited to values between approximately the fifth and ninety-fifth quantiles of the values observed and collected in Table 1.

In the development of the tables of this example, LOESS models were also developed for a 16-hour dissolution, which has a lower release rate range. Prediction intervals (at the 95% confidence level) were calculated for the predicted values of release rate. Lower prediction bounds (at the 95% confidence level) were calculated for 16-hour dissolution. For each combination of PctFines and pan load, the weight gain was selected with the predicted release rate closest to a target of 8.03%/h, provided that the prediction intervals for the release rate and 16-hour dissolution were entirely within the release specifications. Tables 1 and 2 were then created. The rows in Table 1 and Table 2 refer to the PctFines in the active layer for making the tablet. The columns in Table 1 and Table 2 refer to the pan load (Panwts) in kg. The cell corresponding to a particular combination of column and row contains the value of the membrane weight gain (WTGain) or coating thickness that should be applied to the tablet having an active layer, with the PctFines corresponding to the value shown in the row heading, and the pan load corresponding to the value shown in the column heading. This weight gain is applied in production in order to produce a controlled release isradipine tablet having approximately the target release rate.

Controlling the Percentage Fines in the Active Substance Layer

The PctFines in the active substance layer have a significant correlation with the drug release rate of the controlled release tablet. In some implementations, it is important to control the amount of fines in the active substance to a consistent value within a predetermined range. For the embodiment including isradipine as the active substance, it may be important, for example, that the PctFines be maintained between 18%-28%, preferably 20%-25%. More preferably, the PctFines may be maintained near the center of that range. In an exemplary embodiment, the PctFines should be about 22.5%.

The present invention embodies a process and system for manufacturing the drug layer granulation based on the understanding that the current and/or power and/or the amount of PolyFines (i.e., polymer fines in the active layer mixture) used in the granulation process contribute to the PctFines in the active substance layer. This embodiment involves a procedure that may be determined based on the determined current and/or power usage and/or amount of PolyFines.

In the granulation process for producing the drug layer granulation to be included in the controlled release tablet, the active substance and the excipients are mixed in a mixer. A binding agent, such as alcohol, is added. As the mixture thickens, the machine requires more power to move its paddles through the mixture. The PctFines in the active substance produced by the method has a mathematical relationship to the Amperes (Amps) used in mixing the active substance and excipients.

Figure 5:
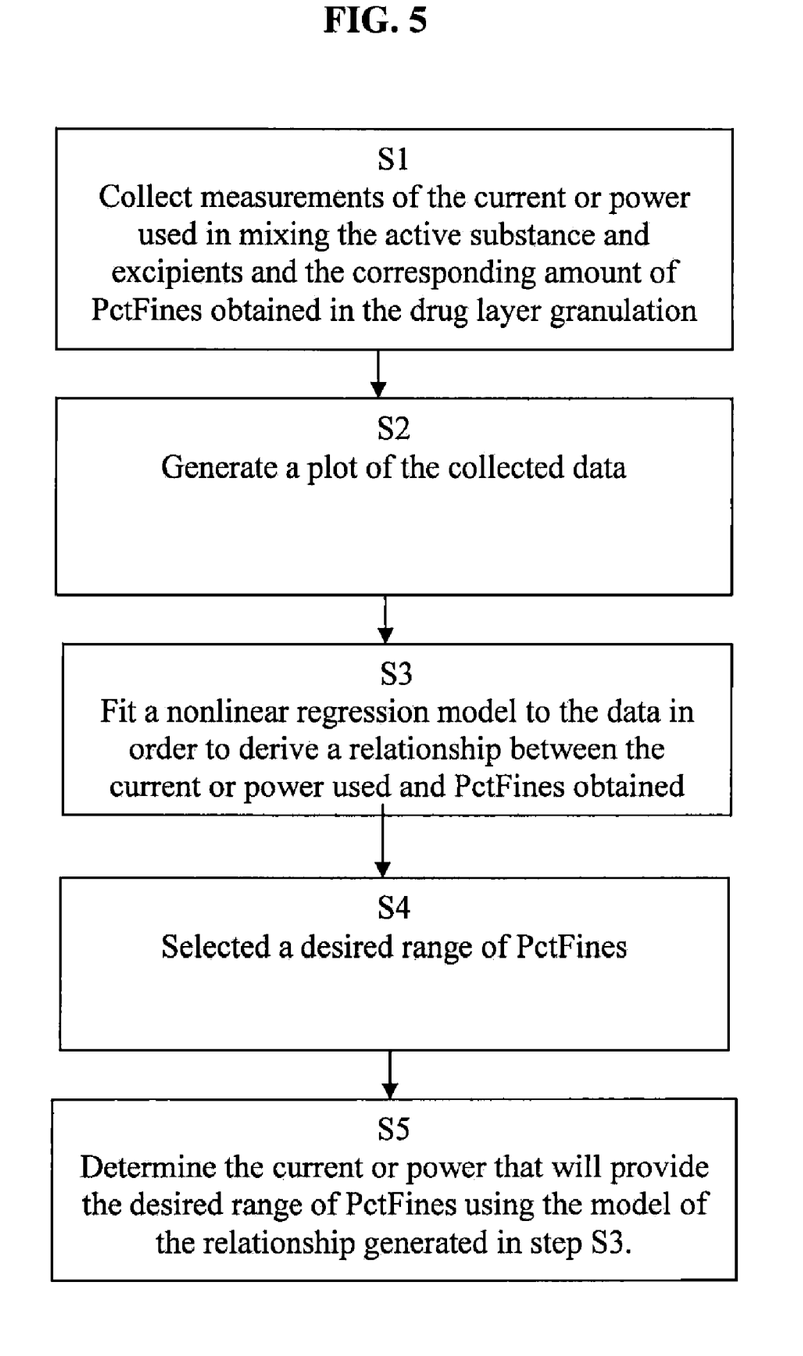
FIG. 5 shows a flow diagram of an exemplary embodiment of a method applying the present invention.
Figure 6:
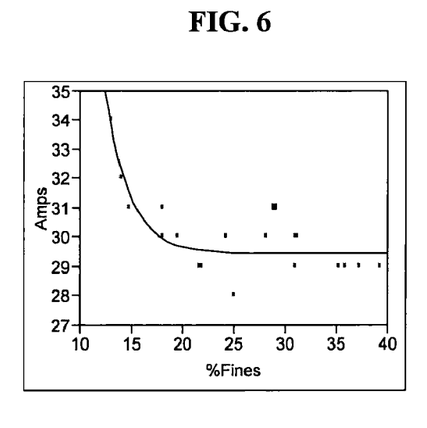
FIG. 6 shows an exemplary plot according to the present invention.
Figure 7:
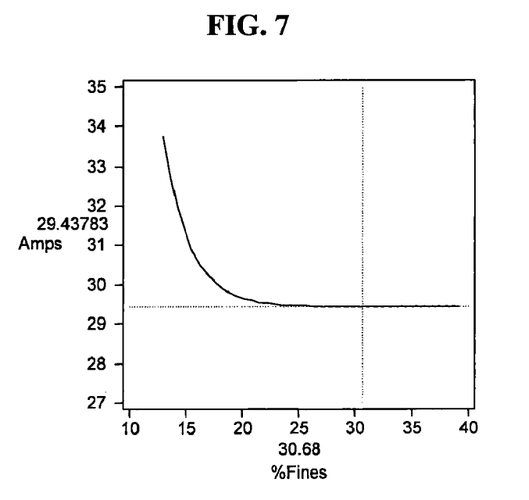
FIG. 7 shows an exemplary plot according to the present invention.

FIG. 5 shows a flow diagram for an exemplary embodiment of a method for obtaining a desired PctFines in the drug granulation, based on Amps needed in the mixing process. In step S1 the PctFines in the finished drug layer granulation and the current or power used in making the drug granulation layer are measured. The measurements are then collected for a plurality of batches of the drug granulation layer. In step S2, a plot is generated for the collected data, with one axis showing the current or power and the other axis showing PctFines. An exemplary embodiment of the plot is shown in FIG. 6. In step S3, a nonlinear model fitting algorithm is used to derive a model of the relationship. In step S4, a preferred range of PctFines is selected. In step S5 the current or power necessary to provide a batch of drug layer granulation having PctFines in the selected range is determined using the derived model from step S3. Thereafter, the determined current or power can be used in order to produce a drug layer granulation having PctFines within the desired range. Of course, other methods may be used besides a plot to correlate power to percentage fines.

In this exemplary embodiment where the drug layer granulation is isradipine and the selected range of PctFines is 20-25%, more preferably about 22.5%, the measurements were plotted and a nonlinear fitting algorithm was applied to generate the plot in FIG. 6. From the plot, it was determined that 29.44 Amps was the lower limit for the formation of fines in the active substance. At 29.44 Amps, the PctFines are greater than 25%. However, below 25% PctFines, the Amps increase exponentially with a linear decrease in PctFines. It was determined that the relationship is described by Equation 1:

$$\text{Amps} = 1093.6 \cdot e^{-0.4258\% \, Fines} + 29.44 \qquad \text{(Equation 1)}$$

It was also determined from the plot that the upper limit of Amps was 29.65 Amps. Thus, in order to control the PctFines within the 20-25% range, the maximum Amps used in mixing the active substance and the excipients should be between about 29.44 Amps and 29.65 Amps. An appropriate amperage at which to stop the granulation process is about 29.5 Amps in order to achieve the preferred target of about 22.5% PctFines.

Figure 8:
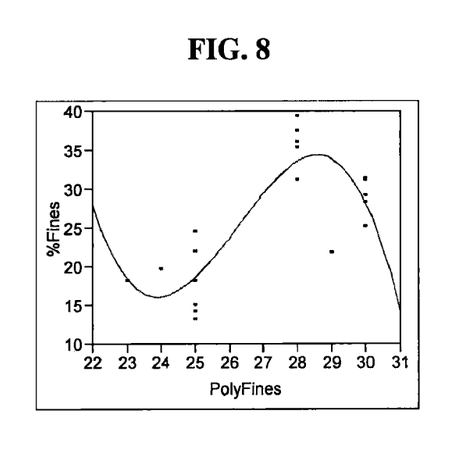
FIG. 8 shows an exemplary plot according to the present invention.
Figure 9:
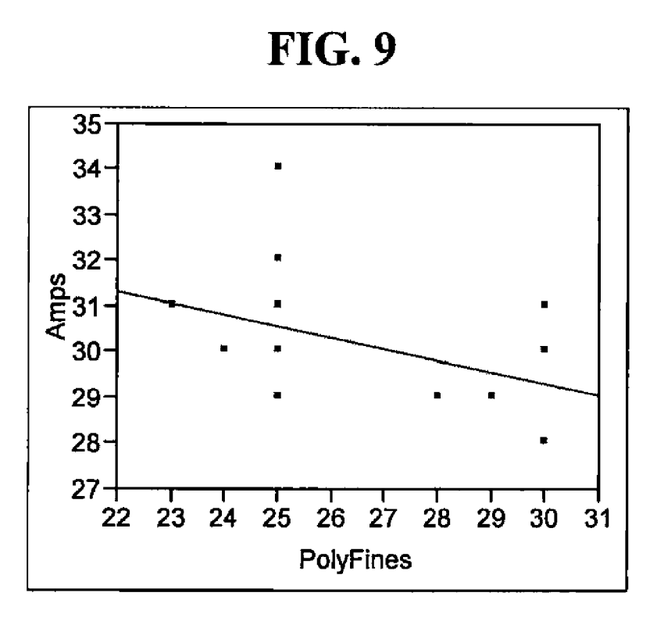
FIG. 9 shows an exemplary plot according to the present invention.

A second factor that influences the PctFines in the drug layer granulation is the PolyFines in the drug layer granulation. The amount of PolyFines and PctFines may be measured for a plurality of batches of the drug layer granulation, and the collected data may be plotted to show the relationship between PolyFines and PctFines. In addition, a plot can be generated to show the relationship between PolyFines and the power used in mixing the active substance and the excipients. Exemplary embodiments of these plots are shown in FIGS. 8 and 9, which were made with data collected on isradipine using a Lodige mixer. FIGS. 8 and 9 show that the amount of PolyFines more significantly affects the PctFines than the amount of PolyFines affects the power used in the granulation process. FIG. 8 shows that the PolyFines affect the PctFines in a cubical function. The regression coefficient of the relationship is about 70% and the relationship of PctFines to PolyFines is statically significant. Thus, the higher PolyFines contribute to higher fines in the drug layer granulation.

In an exemplary embodiment for applying the determined parameters for isradipine, after dry mixing, the mixture is sprayed with 51.36 kg alcohol containing BHT. The mixture is then sprayed with up to 60 kg (46+14) of alcohol until the predetermined 29.5 Amps is achieved. If the amperage does not reach 29.5 Amps, then mixing is continued for up to 90 seconds in an attempt to achieve 29.5 Amps. Then the granulation process is stopped.

Table 6 shows the results of batches of drug layer granulation manufactured according to an embodiment of the present invention using an amperage of 29.5, where the predicted granulation is 22.5%. The average percentage granulation for the 12 batches is 22.34%.

TABLE 6

| Batch | Amperage | PolyOx Lot # | PolyOx (Dow's particle size) | PolyOx Viscosity | Percentage granulation particle size #200 +Fines |
|---|---|---|---|---|---|
| 10021249 | 29.5 | 10021888 | 56/28 | 70 | 19.1 |
| 10021250 | 29.5 | 10021888 | 56/28 | 70 | 21.1 |
| 10022934 | 29.5 | 10021888 | 56/28 | 70 | 22.8 |
| 10022935 | 29.5 | 10021888 | 56/28 | 70 | 23.5 |
| 10022936 | 29.5 | 10021888 | 56/28 | 70 | 22.4 |
| 10022937 | 29.5 | 10021888 | 56/28 | 70 | 24 |
| 10022938 | 29.5 | 10021888 | 56/28 | 70 | 22.6 |
| 10024253 | 29.5 | 10021888 | 56/28 | 70 | 21.6 |
| 10024256 | 29.5 | 10024832 | 58/28, 56/27 | 70, 68 | 21.8 |
| 10024745 | 29.5 | 10024832 | 56/27 | 68 | 23.2 |
| 10024324 | 29.5 | 10024832 | 56/27 | 68 | 21.9 |
| 10024325 | 29.5 | 10024832 | 56/27 | 68 | 24.1 |
| 10024326 | 29.5 | 10024832 | 56/27 | 68 | 25.2 |

While the present invention has been described in connection with various preferred embodiments, it will be understood by those skilled in the art that variations and modifications of the preferred embodiments described above may be made without departing from the scope of the invention. Other embodiments will be apparent to those skilled in the art from a consideration of the specification or from a practice of the invention disclosed herein. It is intended that the specification and the described examples are considered exemplary only.

What is claimed is:

1. A method, comprising:

manufacturing a plurality of oral osmotic drug delivery devices, each of which comprises a bi-layer core comprising (1) an active layer comprising particles of a mixture of a drug and one or more excipients wherein the particles have a particle size distribution as determined by the percentage of the particles that pass through a #120 mesh screen, and (2) an osmotic layer, and a semipermeable outer coating substantially surrounding the bi-layer core;

collecting measurements on the particle size distribution in the active layer, a weight value of a plurality of bi-layer cores, and a weight value of the outer coating used in the manufacturing of the plurality of osmotic drug delivery devices, and determining a release rate for the plurality of osmotic drug delivery devices;

deriving a relational mechanism relating the particle size distribution, the weight value of the plurality of bi-layer cores, and the weight value of the outer coating to obtain a selected release rate using the collected measurements;

selecting at least one parameter of the particle size distribution, the weight value of the plurality of bi-layer cores, and the weight value of the outer coating;

determining at least one of the remaining parameters to obtain the selected release rate in a further plurality of oral osmotic drug delivery devices using the relational mechanism;

manufacturing the further plurality of oral osmotic drug delivery devices utilizing information obtained from the determining step; and administering to a subject at least one of the oral osmotic drug delivery devices.

2. The method according to claim 1, wherein the method further comprises predetermining at least a second parameter of the particle size distribution, the weight value of the plurality of bi-layer cores, and the weight value of the outer coating.

3. The method according to claim 2, wherein the particle size distribution and the weight value of the plurality of bi-layer cores are predetermined and maintained at an approximately constant level, and wherein the selected release rate is obtained by determining a weight value of the outer coating parameter based on the relational mechanism.

4. The method according to claim 1, wherein the method further comprises determining a second parameter of the particle size distribution, the weight value of the plurality of bi-layer cores, and the weight value of the outer coating varies and a variation of a third parameter of the particle size distribution, the weight value of the plurality of bi-layer cores, and the weight value of the outer coating, in order to maintain the selected release rate of the further plurality of oral osmotic drug delivery devices using the relational mechanism.

5. The method according to claim 1, wherein the relational mechanism is derived using a neural network.

6. The method according to claim 1, wherein the relational mechanism is derived using multiple linear regression.

7. The method according to claim 1, wherein the relational mechanism is derived using Monte Carlo simulation.

8. The method according to claim 1, wherein the relational mechanism comprises a table.

9. The method according to claim 1, wherein the drug comprises an antihypertensive drug.

10. The method according to claim 1, wherein the drug comprises isradipine.

11. The method according to claim 1, wherein the selected release rate is about 6.93%/hr to 9.12%/hr of a drug dose set forth in a label claim under the following conditions: USP dissolution test <711>, Apparatus 2, 50 rpm, 0.2% N,N-dimethyl dodecylamine N-oxide (LDAO) or equivalent solvent, temperature 37° C.±0.5° C.

* * * * *